United States Patent [19]

Schneider

[11] Patent Number: 5,693,190

[45] Date of Patent: Dec. 2, 1997

[54] RECOVERY OF GLYCOLS FROM USED ANTIFREEZE COMPOSITIONS BY DISTILLATION

[75] Inventor: Kurt Schneider, Bad Dürkheim, Germany

[73] Assignee: BASF Aktiengesellschaft, Ludwigshafen, Germany

[21] Appl. No.: 549,785

[22] PCT Filed: Jun. 27, 1994

[86] PCT No.: PCT/EP94/02084

§ 371 Date: Dec. 4, 1995

§ 102(e) Date: Dec. 4, 1995

[87] PCT Pub. No.: WO95/01213

PCT Pub. Date: Jan. 12, 1995

[30] Foreign Application Priority Data

Jul. 1, 1993 [DE] Germany ............ 43 21 846.6

[51] Int. Cl.$^6$ ............... B01D 3/34; C07C 29/80
[52] U.S. Cl. ............ 203/6; 203/34; 203/35; 568/868
[58] Field of Search ............ 203/1, 34, 6, 35; 568/868

[56] References Cited

U.S. PATENT DOCUMENTS

| 4,179,328 | 12/1979 | Barra et al. | 203/49 |
| 4,225,394 | 9/1980 | Cox et al. | 568/868 |
| 4,830,712 | 5/1989 | Crandall et al. | 203/35 |
| 5,262,013 | 11/1993 | Beal et al. | 203/1 |
| 5,294,305 | 3/1994 | Craft, Sr. et al. | 203/38 |

FOREIGN PATENT DOCUMENTS

| 193631 | 8/1987 | Japan . |
| 1237243 | 6/1986 | U.S.S.R. . |
| 1641876 | 4/1991 | U.S.S.R. . |

OTHER PUBLICATIONS

Kirk—Othmer, "Encyclopedia of Chemical Technology", 4th Ed. vol. 3, 1991, pp. 365–367.

*Primary Examiner*—Virginia Manoharan
*Attorney, Agent, or Firm*—Oblon, Spivak, McClelland, Maier & Neustadt, P.C.

[57] ABSTRACT

A method for the recovery of glycols from used antifreeze compositions by distillation entails the used antifreeze composition being treated before and/or during its distillation with an effective amount of sulfamic acid.

12 Claims, No Drawings

RECOVERY OF GLYCOLS FROM USED ANTIFREEZE COMPOSITIONS BY DISTILLATION

The invention relates to a method for the recovery of glycols from used antifreeze compositions by distillation.

Large amounts of used antifreeze compositions from combustion engines arise each year. Since these liquids contain considerable amounts, up to 50% by volume, of glycols, especially ethylene glycol and propylene glycol and, in addition, a number of additives such as corrosion inhibitors or antifoam agents (cf. Ullmanns Enzyklopädie der Technischen Chemie, 4th Edition, Volume 12, pages 208–209, Verlag Chemie, Weinheim 1976), these used antifreeze compositions cannot simply be tipped into the sewers but must undergo special disposal or processing. Disposal of antifreeze compositions by incineration consumes considerable energy because of their high water content, which is why this method of disposal is costly and uneconomic.

For this reason a number of methods for recovering glycols from used antifreeze compositions by distillation has been developed, for example the methods disclosed in DE-A 40 30 331 and U.S. Pat. No. 4,080,247. The problem which arises in the distillation of used antifreeze compositions is that thermal decomposition of nitrogenous additives during the distillation results in considerable amounts of gaseous nitrogen oxides $NO_x$ being liberated, and these must not be released to the air for ecological reasons. For this reason it has to date been necessary to extract the liberated nitrogen oxides, for example using a water ring pump, and to purify the effluent polluted in this way by neutralization in the treatment plant. As a consequence of the considerable and costly technical complexity of removing the liberated nitrogen oxides by this method, the recovery of glycols from used antifreeze compositions has remained uneconomic to date.

It is an object of the present invention to find an economic method for recovering glycols from used antifreeze compositions by distillation which does not have the above-mentioned disadvantages.

We have found, after lengthy efforts and after testing a large number of chemical substances, that this object is achieved by a method for recovering glycols from used antifreeze compositions by distillation, wherein the used antifreeze composition is treated before and/or during its distillation with an effective amount of sulfamic acid.

We have found that the treatment, according to the invention, of the antifreeze composition with sulfamic acid of the formula I $$H_2NSO_3H \qquad \text{I}$$

is able completely to suppress the formation of nitrogen oxides during the distillation of antifreeze compositions.

To treat the used antifreeze compositions with sulfamic acid, the used composition is generally treated at from 0° to 150° C., preferably 20° to 100° C. and particularly preferably 50° to 80° C., with, in general, from 1 to 20, preferably 5 to 15 and particularly preferably 5 to 10, g of sulfamic acid per liter of used composition. The treatment of the used composition can take place both in a separate stage preceding the distillation and during the distillation. In the latter case, the sulfamic acid is added to the antifreeze composition, which is then distilled. It is advantageous to establish the optimal amount to be added to specific batches of used antifreeze composition in a simple preliminary test.

The pretreatment, according to the invention, of the used antifreeze compositions is advantageously carried out when the composition has a low pH, in general at pH 1–6, preferably at pH 2–5.5 and particularly preferably at pH 3–4. The pH of the used antifreeze composition can be adjusted, for example, by adding an appropriate amount of sulfamic acid, while the used composition is advantageously acidified with an involatile, non-oxidizing mineral acid, eg. with phosphoric acid or sulfuric acid, to the desired pH, and subsequently the amount of sulfamic acid which is required to prevent nitrogen oxide formation is added to the used antifreeze composition.

The duration of this pretreatment depends on the temperature chosen for the treatment. The required treatment time is generally longer at low temperatures than at elevated temperature.

No special apparatus is needed for the pretreatment. It can be carried out, for example, in storage tanks which are advantageously equipped with stirrers, in open stirred vessels or in tubular reactors.

The recovery of the glycols by distillation from the used antifreeze compositions pretreated in this way can be carried out by prior art distillation methods, for example those disclosed in Ullmanns Enzyklopädie der Technischen Chemie, 4th Edition, Volume 8, pages 201–202, Verlag Chemie, Weinheim 1974; DE-A 40 30 331, U.S. Pat. No. 4,080,247 or DE-A 23 64 151.

The method according to the invention can be used to recover glycols, especially ethylene glycol and propylene glycol, from virtually all commercial antifreeze compositions.

The sulfamic acid required for the method according to the invention can be obtained, for example, by reacting urea with fuming sulfuric acid by the method described in Brauer, Handbuch der Präparativen Anorganischen Chemie, pages 455–456, Enke, Stuttgart 1960.

EXAMPLE 2000 g of a used antifreeze composition which contains ethylene glycol and has a water content of about 60% by weight were stirred with 16 g of 85% strength phosphoric acid and 5 g of sulfamic acid at 20° C. for about 5–6 hours. Subsequently the water was removed as completely as possible by distillation under 200–300 mbar. The ethylene glycol Solution concentrated in this way was then fractionally distilled under 1–10 mbar resulting in recovery of 590 g of ethylene glycol. No nitrogen oxides were produced during the distillation.

We claim:

1. A method for recovering glycols from used antifreeze compositions by distillation, comprising treating the used antifreeze composition before and/or during its distillation with an effective amount for suppressing the formation of nitrogen oxides during the distillation, of sulfamic acid.

2. The method as claimed in claim 1, wherein the treatment of the used antifreeze composition with sulfamic acid is carried out at pH 1–6.

3. The method as claimed in claim 2, wherein the pH is 2–5.5.

4. The method of claim 3, wherein the pH is 3–4.

5. The method of claim 2, wherein the pH is obtained by adding a non-oxidizing mineral acid.

6. The method of claim 5, wherein the non-oxidizing mineral acid is phosphoric acid or sulfuric acid.

7. The method as claimed in claim 1, wherein the sulfamic acid is present in an amount of 1 to 20 g per liter of used antifreeze composition.

8. The method as claimed in claim 7, wherein the amount is 5 to 15 g per liter.

9. The method as claimed in claim 8, wherein the amount is 5 to 10 g per liter.

10. The method as claimed in claim 1, wherein the treating is carried out at from 0° to 150° C.

11. The method as claimed in claim 10, wherein the treating is carried out at from 20° to 100° C.

12. The method as claimed in claim 11, wherein the treating is carried out at from 50° to 80° C.

* * * * *